United States Patent [19]

Kume et al.

[11] Patent Number: 4,770,875

[45] Date of Patent: Sep. 13, 1988

[54] **PROCESS FOR PREPARATION OF IMPROVED MUTANT STRAIN OF *BORDETELLA BRONCHISEPTICA* USEFUL FOR LIVE ATTENUATED VACCINE FOR PROTECTION OF *B. BRONCHISEPTICA* INFECTION AND LIVE ATTENUATED AR VACCINE PRODUCED THEREFROM**

[75] Inventors: Katsumi Kume, Chiba; Toyotsugu Nakai, Kanagawa; Hiroshi Nishizawa, Chiba; Takashi Yoshikawa, Aomori; Hirofumi Danbara, Tokyo, all of Japan

[73] Assignee: The Kitasato Institute, Tokyo, Japan

[21] Appl. No.: 119,075

[22] Filed: Nov. 10, 1987

[30] Foreign Application Priority Data

Nov. 27, 1986 [JP] Japan .................................. 61-280890

[51] Int. Cl.$^4$ ......................... A61K 39/10; C12N 1/00; C12N 15/00
[52] U.S. Cl. .................................. 424/92; 435/172.1; 435/253
[58] Field of Search ................ 424/92; 435/172.1, 253

[56] References Cited

U.S. PATENT DOCUMENTS

| | | | |
|---|---|---|---|
| 4,016,253 | 4/1977 | Switzer et al. | 424/92 |
| 4,225,583 | 9/1980 | Switzer et al. | 424/92 |
| 4,456,588 | 6/1984 | Shimizu | 424/92 |
| 4,530,832 | 7/1985 | Goodnow et al. | 424/92 |

FOREIGN PATENT DOCUMENTS

0072656 8/1981 European Pat. Off. ......... 435/172.1

OTHER PUBLICATIONS

"Dermonecrotic Activity of Pasteurella multocida Strains Isolated from Pigs in Japanese Fields", Accepted Dec. 1, 1983, by A. Sawata et al., pp. 141–148.

"Characterization of Dermonecrotic Toxin Produced by Serotype D Stains of Pasteurella Multocida", *American Journal of Veterinary Research*, vol. 45, No. 11, by T. Nakai et al., pp. 2410–2413.

"Intracellular Locations of Dermonecrotic Toxins in Pasteurella Multocids and in Bordetella Bronchiseptica", *American Journal of Veterinary Research*, vol. 46, No. 4, by T. Nakai et al., pp. 870–874.

"Properties of Dermonecrotic Toxin Prepared from Sonic Extracts of Bordetella bronchiseptica", *Infection and Immunity*, vol. 52, No. 4, May 1986, by K. Kume et al., pp. 370–377.

*Primary Examiner*—Howard E. Schain
*Attorney, Agent, or Firm*—Young & Thompson

[57] ABSTRACT

A process for the preparation of a mutant strain of *B. bronchiseptica* having chromosomal genetic markers carrying at least temperature-sensitive (grown at 42° C.), nalidixic acid-resistant and heat-labile dermonecrotic toxin producing ability negative markers, suitable for the preparation of live attenuated AR vaccine, which comprises subjecting a strain of *B. bronchiseptica* to an induced mutation, isolating a mutant having the genetic markers of being at least temperature-sensitive (grown at 42° C.), nalidixic acid-resistant and heat-labile dermonecrotic toxin negative, culturing the isolated strain of *B. bronchiseptica* on a Bordet-gengou agar plate containing nalidixic acid at 42° C., thereafter picking up an organism morphologically resembling a phase-I organism, repeating the procedures of culturing and picking up, and converting the organisms to a heat-labile dermonecrotic toxin-producing ability negative phase-I organism having a complete capsular antigen.

7 Claims, No Drawings

PROCESS FOR PREPARATION OF IMPROVED MUTANT STRAIN OF *BORDETELLA BRONCHISEPTICA* USEFUL FOR LIVE ATTENUATED VACCINE FOR PROTECTION OF *B. BRONCHISEPTICA* INFECTION AND LIVE ATTENUATED AR VACCINE PRODUCED THEREFROM

BACKGROUND OF THE INVENTION

This invention relates to a process for the preparation of an improved mutant strain of *Bordetella bronchiseptica* having strong immunogenicity and low virulence, which is suitable for the preparation of *B. bronchiseptica* live attenuated vaccines. The present invention also relates to a live vaccine prepared from *B. bronchiseptica*.

*Bordetella bronchiseptica* has been known to cause respiratory disease in various animals such as swine, dogs, rabbits, guinea pigs and mice. Infection with the organisms in neonatal pigs causes swine atrophic rhinitis (hereinafter designated as AR) which induces nasal turbinate atrophy and results in growth delay and a decrease of the feed consumption ratio. This is a serious problem in the livestock industry. A killed AR vaccine has been commercialized for the prophylaxis of swine AR; however, the effectiveness of the vaccine is limited.

Recently, a live attenuated AR vaccine was developed and reported by Shimizu et al. (U.S. Pat. No. 4,456,588). However, the organisms involved in this live vaccine can grow only at 34°–37° C. Also, these organisms are slow to form colonies on a solid medium and show poor colonization on the nasal mucosa of swine, and also show no serum antibody production when inoculated in pigs.

At least 10–14 days are necessary to obtain the immunologic effects of killed AR vaccine after administration. Therefore, a vaccine with strong immunity at an early infant stage has long been sought. *B. bronchiseptica* has generally been known to grow at 32°–37° C. ("Atrophic Rhinitis of Swine Bordetella Infectious Disease", Ed. M. Ogata, Buneido Publ. Co., 1979). And the fact that pathogenic bacteria lose their virulence, when cultured at a high temperature, is also known.

In order to obtain mutant strains of *B. bronchiseptica* for the production of live AR vaccine, we have considered the above phenomena, and have devised the present invention which includes a process for the preparation of an improved mutant strain of *B. bronchiseptica* having strong immunity and low virulence, and a live attenuated AR vaccine prepared therefrom.

OBJECTS OF THE INVENTION

An object of the present invention is to provide a process for the preparation of an improved mutant strain of *B. bronchiseptica* having strong immunogenicity and low virulence, which is suitable for the preparation of a live attenuated AR vaccine.

Another object of the present invention is to provide a mutant strain of *B. bronchiseptica* having chromosomal genetic markers of being at least temperature-sensitive (grown at 42° C.), nalidixic-acid resistant and dermonecrotic toxin (hereinafter designated as DNT)-producing ability negative (hereinafter designated as DNT negative) markers.

A further object of the present invention is to provide a process for the preparation of a mutant strain of *B. bronchiseptica* which comprises subjecting a strain of *B. bronchiseptica* to an induced mutation, isolating a mutant having the genetic markers of being at least temperature-sensitive (grown at 42° C.), nalidixic acid-resistant and DNT negative, culturing the strain of *B. bronchiseptica* on Bordet-gengou (hereinafter designated as BG) agar plate containing nalidixic acid at 42° C., thereafter picking up an organism morphologically resembling phase-I, repeating the procedures of a cultivation on the BG agar plate and the picking up of phase-I organisms, and converting the organisms to DNT negative phase-I organism having a complete capsular antigen.

A still further object of the present invention is to provide a live attenuated AR vaccine comprising phase-I organism *B. bronchiseptica* having at least the genetic markers of temperature-sensitivity (grown at 42° C.), nalidixic acid resistance and DNT negative markers.

According to the present invention, a mutant strain of *B. bronchiseptica* can be obtained by inoculating the naturally isolated parent, wild or virulent strain of *B. bronchiseptica* on BG agar plate containing 200 μg/ml of nalidixic acid, culturing the plate at 42° C., picking up the grown colonies, subculturing the picked up colonies on the same plate and repeating the procedure of picking up the colonies and subculture thereof under the same conditions as recited hereinabove.

In the above procedure, when a good growth is observed on BG agar plate containing nalidixic acid at 42° C., the mutant strain can be selected by examining the DNT-producing ability of the colonies grown on the plate using a guinea pig skin test, picking up the colonies showing DNT negative, subculturing the same, and repeating the above procedure under the same conditions as recited hereinabove.

Examples of the starting strain used in the present invention are a wild strain of *B. bronchiseptica* such as strain B-001 identified hereinbelow or a laboratory stock culture such as strain L3.

Strain B-001 is obtained from the cultivation of a cotton swab sample collected from the nasal cavity of a pig affected with AR, in which the sample is streaked on a BG agar plate and cultured at 37° C. for two days, and the thus-obtained colonies of *B. bronchiseptica* are selected by checking the properties which were described hereinbefore.

The mutant strain of the present invention, which has the genetic markers of being temperature-sensitive (grown at 42° C.), nalidixic acid-resistant, and DNT negative, can be produced by a conventional method of inducing mutation. Namely, a strain B-001 is inoculated on a BG agar plate containing 200 μg/ml of nalidixic acid and cultured at 42° C. for 7 days. The colonies grown on the agar plate, which morphologically resemble a phase-I organism, are picked up, inoculated on a fresh BG agar plate containing nalidixic acid and cultured at 42° C. for 3–5 days. After repeating the procedure of picking up the organisms, culturing them and selecting the colonies showing DNT negative by a guinea pig skin test, there can be isolated the mutant strain which is DNT negative and temperature-sensitive (grown at 42° C.). The strain is designated as strain B-42 and is suitable for the production of a live attenuated AR vaccine for the prophylaxis of *B. bronchiseptica* infection in swine.

This mutant strain B-42 of *B. bronchiseptica* was deposited in The Fermentation Research Institute in the permanent culture collection thereof and was assigned FERM P-9038. The said strain possesses chromosomal genetic markers having the properties of being temperature-sensitive (grown at 42° C.), nalidixic acid-resistant and DNT negative, and moreover the strain has a sufficient amount of capsular antigen which is essential in a live attenuated AR vaccine and significantly low virulence and strong immunogenicity.

Accordingly, the strain B-42 is particularly useful for the production of a live attenuated AR vaccine for the prevention of *B. bronchiseptica* infection in swine.

The strain B-42 used in the present invention has the following specific features and properties:

Biological properties of the strain B-42, strain B-001 (wild strain from pigs affected with swine AR), strain L3 for the production of killed AR vaccine (stock culture), and strain ATCC 4617 (stock culture) are examined according to the methods described by Cowan et al. (Cowan, S. T. and Steel, K. J.: Manual for the Identification of Medical Bacteria, 2nd Ed., Cambridge Univ. Press, England, 1974) and the results are shown in Table 1, in which the strain B-42 has the same properties as strain B-001, strain L3 and strain ATCC 4617, except for high temperature adaptability and hemolytic activity.

TABLE 1

| Properties | Strain | | | |
|---|---|---|---|---|
| | B-42 | B-001 | L3 | ATCC 4617 |
| Gram-staining | Negative | Negative | Negative | Negative |
| Motility | + | + | + | + |
| Glucose fermentation | − | − | − | − |
| Indole production | − | − | − | − |
| Methyl red test | − | − | − | − |
| VP test | − | − | − | − |
| Citrate utilization | + | + | + | + |
| Nitrate reduction | + | + | + | + |
| Urea hydrolysis | + | + | + | + |
| Oxidase reduction | + | + | + | + |
| KCM test | + | + | + | + |
| Lysine decarboxylation test | + | + | + | + |
| Catalase reduction | + | + | + | + |
| Hemolysis(horse RBC) | | | | |
| 20% | − | + | + | + |
| 5% | $(\pm)^a$ | + | + | + |
| Growth on BG-agar plate at | | | | |
| 37° C. | + | + | + | + |
| 42° C. | + | $(\pm)^b$ | $(\pm)^b$ | $(\pm)^b$ |
| Growth on BG-agar plate containing nalidixic acid (200 μg/ml) at | | | | |
| 37° C. | + | − | − | − |
| 42° C. | + | − | − | − |

[a] Weak hemolysis
[b] Poor growth (little colony formation)

A.

BIOLOGICAL PROPERTIES

1. Temperature sensitivity:

Strain B-42 (mutant strain) shows maximum growth for 2-3 days at 37° C. and for 4-5 days at 42° C., whilst B-001, L3 and ATCC 4617 strains (virulent strains) show maximum growth for 2 days at 37° C. but very small colonies (less than 1 mm in diameter) are formed in 7 days at 42° C. Growth conditions at 42° C. thus can be a marker for the differentiation of mutant strain B-42 from wild and stock strains.

2. Hemolysis:

Strain B-42 lacks hemolytic activity on horse erythrocytes or has weak hemolytic activity depending upon the concentration of erythrocytes on a BG agar plate. On the other hand, B-001, L3 and ATCC 4617 strains show strong hemolytic activity, which can thus also be a marker for differentiation of strain B-42 from wild and stock strains.

3. Nalidixic acid-sensitivity:

Strain B-42 shows good growth on a BG agar plate containing nalidixic acid at 37° C. and 42° C., while B-001, L3 and ATCC 4617 strains are sensitive to nalidixic acid.

The minimum growth inhibitory concentration of nalidixic acid for strain B-42 is over 200 μg/ml, and since in general the wild and stock strains of *B. bronchiseptica* so resistant to nalidixic acid are very few (refer to Ogata's reference hereinbefore), nalidixic acid resistance can also be a good marker for the differentiation of a mutant strain B-42 from wild and stock strains. Cultivation of a BG agar plate containing nalidixic acid at 42° C. thus tends to confirm a differentiation made by any of the other techniques above.

4. DNT-producing ability:

Phase-I organisms of *B. bronchiseptica* produce DNT and the DNT is known as a virulent factor of this organism. The said toxin participates nasal turbinate atrophy in young pigs and in young mice infected with the bacteria. (Hanada, M., Shimoda, K., Tomita, S., Nakase, Y. and Nishiyama, Y., "Production of Lesions Similar to Naturally Occurring Swine Atrophic Rhinitis by Cell-free Sonicated Extract of *Bordetella bronchiseptica* of Pig Origin", Japan. J. Vet. Sci., 41: 1-8, 1979). Therefore, a strain deficient in DNT-producing ability is essential for the preparation of a live attenuated AR vaccine.

The DNT-producing ability of a mutant strain B-42 is compared with those of the wild strain (B-001) and the vaccine strain (L3). A bacterial suspension of each strain ($5 \times 10^{11}$ cells/ml) is sonicated at 10 KHz for 10 mins. (Soniator, Ohtake Works, Tokyo, 150W) in a cold water bath and the sonicate is centrifuged at 10,000 g for 60 mins., and then filtered through a 0.22 μm Millipore filter to prepare test samples. Two-fold serial dilutions of the test samples are made with distilled water. Hartley guinea pigs weighing about 300 g were injected intradermally with portions (0.1 ml) of two-fold dilutions. The titers of the samples were the reciprocal of the highest dilution showing a positive necrotic lesion more than 5 mm in diameter observed at 48 hours after injection.

The results are shown in Table 2.

TABLE 2

| | Dermonecrotic Activity |
|---|---|
| Strains | Dermonecrotic titer |
| B-42 (mutant) | <2 |
| B-001 (wild) | 8.192 |
| L3 (vaccine) | 8.192 |

As shown in Table 2, strain B-42 completely lacks DNT-producing ability, which property is confirmed as stable when the strain is subcultured on BG agar plates or passaged through mice over 40 times (Table 3).

TABLE 3

Effect of Passage of Dermonecrotic Titer of Strain B-42

| Passage | Dermonecrotic titer | |
|---|---|---|
| | Subcultured on BG agar plates | Passaged through mice |
| Original strain | <2 | <2 |
| 10 passages | <2 | <2 |
| 20 passages | <2 | <2 |
| 30 passages | <2 | <2 |
| 40 passages | <2 | <2 |

5. Lethal toxicity for mice:

*B. bronchiseptica* shows strong lethal toxicity for mice (Ogata, supra). The lethal toxicity of strain B-42 for mice is compared with that of vaccine strain L3.

Specific-pathogen free (hereinafter designated as SPF) mice (20 mice in one group), 3 weeks of age, were intraperitoneally inoculated with strain B-42 or strain L3 ($1 \times 10^5$ to $1 \times 10^{10}$ cells/mouse), and observed for one week. The dead mice were autopsied immediately after death and their lungs were macroscopically observed. Bacteria were recovered from their lung tissues. The surviving mice were killed one week after inoculation, their lungs were observed and bacteria were recovered from their lung tissues.

As is shown in Table 4, strain B-42 lacks lethal toxicity for mice. This property does not change upon 40 passages of the strain B-42 through mice as compared with that of the original strain. This shows the stable nature of the strain B-42. The dead mice that succumbed to sepsis or pneumotic lesions were observed. No macroscopic changes were observed in the surviving mice.

TABLE 4

Lethal Toxicity for Mice

| Number of inoculated bacteria/mouse | Strain B-42 | Strain L3 |
|---|---|---|
| $1 \times 10^{10}$ | 0/20* | 20/20* |
| $1 \times 10^9$ | 0/20 | 20/20 |
| $1 \times 10^8$ | 0/20 | 20/20 |
| $1 \times 10^7$ | 0/20 | 12/20 |
| $1 \times 10^6$ | 0/20 | 4/20 |
| $1 \times 10^5$ | 0/20 | 0/20 |

*Number of dead mice/Number of inoculated mice

The above results indicate that strain B-42 is quite safe for use in a live AR vaccine.

B.

SEROLOGICAL PROPERTIES

Anti-B-42, anti-L3 and anti-B-001 hyperimmune rabbit sera or anti-B-42, anti-L3 and anti-B-001 hyperimmune swine sera, which are prepared by highly immunizing rabbits or swine with phase-I organisms of strains B-42, L3 and B-001, respectively, are subjected to an agglutination test by using as an antigen consisting of phase-I organisms of strain B-42, phase-I organisms of strain B-001, phase-I organisms of strain L3 and a commercially available AR antigen (AR antigen "Kitasato") (Ogata, supra).

The results are shown in Table 5.

TABLE 5

Agglutinability of Strains B-42, B-001 and L3 Against Hyperimmune Sera Prepared with Homologous Strains

| Antigen (Phase I organisms) | Hyperimmune serum | | | | | |
|---|---|---|---|---|---|---|
| | Strain B-42 | | Strain L3 | | Strain B-001 | |
| | Rabbit | Swine | Rabbit | Swine | Rabbit | Swine |
| Strain B-42 | 20,480 | 10,240 | 20,480 | 10,240 | 20,480 | 10,240 |
| Strain B-001 | 20,480 | 10,240 | 20,480 | 10,240 | 20,480 | 10,240 |
| Strain L3 | 20,480 | 10,240 | 20,480 | 10,240 | 20,240 | 10,240 |
| AR-antigen [Kitasato] | 20,480 | 10,240 | 20,480 | 10,240 | 20,480 | 10,240 |

As is clear from the above results, strain B-42 has the same antigenicity as strain B-001 and strain L3. Furthermore, the agglutinability of strain B-42 subcultured on BG agar plate for 40 passages is not changed as compared with that of an original strain. These results show the stable nature of the strain B-42.

C.

PROTECTION TEST AND SAFETY EVALUATION OF LIVE ATTENUATED VACCINE PREPARED FROM STRAIN B-42

The protective value of a live AR vaccine prepared from the strain B-42 in mice is tested as follows:

SPF mice, 3 weeks of age, are divided into immunized and control groups.

Strain B-42 cultured on BG agar plate at 37° C. for 3 days is suspended in phosphate-buffered saline solution (pH 7.0) to prepare the cell suspension of Table 6. Aliquot portions of the cell suspensions (0.1 ml) are intraperitoneally inoculated into mice, 30 mice in one group. Three weeks after inoculation, aliquot portions of a cell suspension (0.1 ml) of phase-I organisms of strain L3 in phosphate-buffered saline solution (pH 7.0), which is cultured on BG agar plate at 37° C. for 2 days, are intraperitoneally introduced into mice, 20 mice in each group consisting of immune and control groups. The animals are observed for 2 weeks after inoculation. At the time of this introduction, 10 mice in each group are killed and agglutination titers of sera are measured using AR-antigen "Kitasato".

The results are shown in Table 6.

As is shown in Table 6, in the immunized groups which are inoculated with strain B-42 in the amount of more than $10^7$ cells/mouse, all the animals survived without manifesting clinical symptoms, and furthermore, no macroscopic changes are observed upon autopsy 2 weeks after inoculation. In the $10^6$ and $10^5$ cells/mouse inoculated groups, 4 and 5 mice, respectively, are killed after inoculation, and the remainder all survived.

TABLE 6

Protection Test in Mice

| Mice | Immunizing dose of strain B-42 Cells/0.1 ml/mouse | Challenge exposure dose of strain L3 Cells/0.1 ml/mouse | No. of dead mice/ No. of test mice | Geometric mean of agglutination titers of ten mice in each group |
|---|---|---|---|---|
| Immunized group | $1 \times 10^{10}$ | | 0/20 | 1,664 |
| | $1 \times 10^9$ | | 0/20 | 1,216 |
| | $1 \times 10^8$ | $1 \times 10^8$ | 0/20 | 448 |
| | $1 \times 10^7$ | | 0/20 | 40 |
| | $1 \times 10^6$ | | 4/20 | 10 |

TABLE 6-continued

| | Protection Test in Mice | | | |
|---|---|---|---|---|
| Mice | Immunizing dose of strain B-42 Cells/0.1 ml/mouse | Challenge exposure dose of strain L3 Cells/0.1 ml/mouse | No. of dead mice/ No. of test mice | Geometric mean of agglutination titers of ten mice in each group |
| | $1 \times 10^5$ | | 5/20 | 5 |
| Control group | — | $1 \times 10^8$ | 20/20 | <5 |

Agglutination titers are increased depending on the immunizing doses. In the control group, all 20 animals were killed by sepsis and large numbers of inoculated bacteria were found in various organs of all the mice.

As demonstrated hereinabove, strain B-42 of the present invention shows superior immunity against *B. bronchiseptica* infection in mice with great safety.

Strain B-42 of the present invention has specific chromosomal genetic markers, and is superior in immunogenicity and safety, and hence is useful for the production of a live attenuated AR vaccine for the prophylaxis of *B. bronchiseptica* infection in swine.

The live attenuated AR vaccine for prophylaxis of *B. bronchiseptica* infection in swine can be produced by a conventional method for live attenuated vaccines, but using strain B-42. Namely, strain B-42 cultured on BG agar plate at 37° C. is inoculated into a liquid medium for vaccine production and the material is cultured at 37° C.

The cultured cells are collected by centrifugation, mixed with a conventional protective agent for drying, such as 10% skim milk and 5% peptone (the cell suspension:protecting agent=1:1 v/v) and divided into vials and lyophilized to produce a live vaccine preparation. The product is dissolved with an appropriate diluent when used and the solution is administered via the nasal route or inoculated intramuscularly into animals.

The following examples illustrate the present invention but are not to be construed as limiting:

EXAMPLE 1

Preparation of mutant strain

*Bordetella bronchiseptica* strain B-001, inoculated on BG agar plate containing 200 μg/ml of nalidixic acid, was cultured at 42° C., and the colony grown on the plate was selected and was sub-cultured on the same plate. This procedure was repeated under the same conditions. DNT-negative organisms were selected by the guinea pig skin test to obtain a mutant strain which is the said strain B-42, from among the phase-I-like colonies having the ability to grow at 42° C.

EXAMPLE 2

In the method according to Example 1, strain B-001 was replaced by wild strains to obtain a mutant strain of *B. bronchiseptica* for the preparation of live attenuated AR vaccine.

EXAMPLE 3

Strain B-42 prepared according to Example 1 was inoculated on a BG agar plate and cultured at 37° C. for 2 days. This seed culture was inoculated into a liquid medium, cultured at 37° C., and the cultured cells were collected and suspended in a sterilized phosphate-buffered saline solution (pH 7.0) to prepare a bacterial suspension ($4.0 \times 10^{10}$ cells/ml). This cell suspension was mixed well with an equal volume of a protective agent for drying (a mixture of 10% skim milk and 5% peptone solution, which was sterilized at 110° C. for 10 mins.) to prepare the final bulk product. Aliquot portions (2 ml) thereof were introduced into vials, lyophilized and sealed under vaccum to obtain the live vaccine dry product. When the product was kept dark and cool at 2°-5° C., the properties thereof remained quite stable. The product can easily be dissolved homogeneously in sterile phosphate-buffered saline solution (pH 7.0). When the product was dissolved in 20 ml of such a vehicle, the solution contained live bacteria showing a viable count of more than $1 \times 10^8$ cells/ml.

The following examples illustrate the effect of the live attenuated AR vaccine of the present invention.

EXAMPLE 4

A safety evaluation of the strain B-42 obtained in Example 1 was performed using SPF pigs which were divided into three groups, wherein in two groups the live attenuated AR vaccine (1.0 ml) was intranasally given in an amount of $1 \times 10^{10}$ cells and $1 \times 10^8$ cells, respectively, and in the third control group no bacteria was given (each group: two animals). After 15 days, all the animals were sacrificed and autopsied. During the observation period prior thereto, no abnormal clinical signs were observed in any of the animals; and also no abnormal symptoms were macroscopically or histologically observed posthumously in various organs of these animals. In conclusion, strain B-42 is not toxic for pigs.

EXAMPLE 5

A live AR vaccine was dissolved in a sterile phosphate-buffered saline solution (pH 7.0) and further diluted with the same solution in a series of 10-fold dilutions. The immunogenicity of the vaccine in a concentration of $10^4$ cells/ml, $10^6$ cells/ml and $10^8$ cells/ml was tested by using SPF pigs.

Twelve SPF neonatal pigs, 3 days of age, which were negative for antibodies against *B. bronchiseptica,* were divided into four groups (three immunized groups and one control group), three animals per group, wherein in three groups the vaccine (1 ml per animal) was intranasally given and in another group no vaccine was given. Three weeks after the inoculation, all animals were exposed to *B. bronchiseptica* strain L3 (virulent strain), $1 \times 10^7$ cells/ml/pig via the nasal route. Ten weeks after exposure, all the animals were sacrificed and subjected to autopsy.

During the experimental period, no animals of the vaccinated groups showed abnormal clinical symptoms, and the nasal turbinate bones of all the animals were normal, except that two pigs of a group immunized with $1 \times 10^4$ cells/pig showed slight turbinate atrophy. In the unvaccinated control group, all the animals showed clinical symptoms such as eye patch and sneezing, and retardation in growth was observed. Severe nasal turbinate atrophy was observed in all the animals of the unvaccinated group by autopsy. It was thus confirmed that the vaccine gave effective protection in pigs against *B. bronchiseptica.*

EXAMPLE 6

Strain B-42 was tested using SPF pigs negative for antibodies against *B. bronchiseptica,* to determine whether virulence could be reversed. SPF neonatal pigs, 3 days of age, were intranasally inoculated with the live AR vaccine (1 ml/pig, $1\times10^{10}$ cells/ml). After observation for one week, the nasal cavities of the pigs were swept with sterile cotton swabs which had been immersed in 1.5 ml sterile phosphate-buffered saline solution to prepare a suspension of swept bacteria. One milliliter of the suspension was inoculated into other neonatal pigs, and another 0.5 ml was used for checking the taxonomical findings of microbes and counting the number of cells. The procedure was repeated three times (two pigs were used in each procedure).

No abnormal clinical symptoms were found during the observation and no abnormal findings were observed upon autopsy. The inoculated bacteria were found to have good growth in the nasal cavities.

As illustrated hereinabove, strain B-42 was found not to revert to virulent microbes, and was thus further confirmed as to the stability of its properties.

What we claim is:

1. A process for the preparation of a mutant strain of *B. bronchiseptica* having chromosomal genetic markers carrying at least temperature-sensitive (grown at 42° C.), nalidixic acid-resistant and heat-labile dermonecrotic toxin producing ability negative markers suitable for the preparation of live attenuated AR vaccine, which comprises subjecting a strain of *B. bronchiseptica* to an induced mutation, isolating a mutant having the genetic markers of being at least temperature-sensitive (grown at 42° C.), nalidixic acid-resistant and heat-labile dermonecrotic toxin negative, culturing the isolated strain of *B. bronchiseptica* on a Bordet-gengou agar plate containing nalidixic acid at 42° C., thereafter picking up an organism morphologically resembling a phase-I organism, repeating the procedures of culturing and picking up, and converting the organisms to a heat-labile dermonecrotic toxin-producing ability negative phase-I organism having a complete capsular antigen.

2. A process according to claim 1, wherein said subjection to induced mutation comprises a combination of high temperature treatment at 42° C. and treatment with nalidixic acid.

3. A process according to claim 1, wherein the operations of cultivation of Bordet-gengou agar plate containing nalidixic acid and of picking up a colony resembling a phase-I organism are repeated a plurality of times.

4. A process according to claim 1, wherein the starting strain of *B. bronchiseptica* is a strain which is temperature-sensitive (grown at 42° C.), nalidixic acid-resistant and heat-labile dermonecrotic toxin-producing ability negative.

5. A process according to claim 1, wherein the parent strain of said *B. bronchiseptica* is a wild strain isolated from the nasal cavity of pigs infected with *B. bronchiseptica.*

6. A process according to claim 1, wherein the live attenuated AR vaccine is administered to the animals via the nasal route or injected intramuscularly.

7. A live attenuated AR vaccine for the prophylaxis of *B. bronchiseptica* infection, which comprises *B. bronchiseptica* phase-I organisms of strain B-42 having the chromosomal genetic markers of being temperature-sensitive (grown at 42° C.), nalidixic acid-resistant and heat-labile dermonecrotic toxin negative.

* * * * *